(12) United States Patent
Ahnen et al.

(10) Patent No.: US 12,196,892 B2
(45) Date of Patent: Jan. 14, 2025

(54) COMPUTER-IMPLEMENTED METHOD FOR IDENTIFYING AND LOCALIZING RADIATION EVENTS AND A PIXILATED RADIATION DETECTOR FOR CARRYING OUT THE METHOD

(71) Applicant: ETH Zurich, Zurich (CH)

(72) Inventors: Max Ludwig Ahnen, Zürich (CH); Jannis Nikolaus Rudolf Fischer, Zürich (CH)

(73) Assignee: ETH Zurich, Zurich (CH)

( * ) Notice: Subject to any disclaimer, the term of this patent is extended or adjusted under 35 U.S.C. 154(b) by 167 days.

(21) Appl. No.: 17/797,316

(22) PCT Filed: Feb. 3, 2021

(86) PCT No.: PCT/IB2021/050850
§ 371 (c)(1),
(2) Date: Aug. 3, 2022

(87) PCT Pub. No.: WO2021/156752
PCT Pub. Date: Aug. 12, 2021

(65) Prior Publication Data
US 2023/0063565 A1  Mar. 2, 2023

(30) Foreign Application Priority Data
Feb. 5, 2020  (EP) ..................... 20155592

(51) Int. Cl.
*G01T 1/20* (2006.01)
*A61B 6/42* (2024.01)
(52) U.S. Cl.
CPC .......... *G01T 1/2018* (2013.01); *A61B 6/4208* (2013.01)
(58) Field of Classification Search
None
See application file for complete search history.

(56) References Cited

U.S. PATENT DOCUMENTS

2016/0187497 A1* 6/2016 Lerche .................. G01T 1/1647
250/362
2019/0282186 A1 9/2019 Feng et al.

FOREIGN PATENT DOCUMENTS

| CN | 109727226 A | 5/2019 |
| EP | 3 033 636 A1 | 6/2016 |
| WO | 2015/022354 A1 | 2/2015 |

OTHER PUBLICATIONS

Wei et al., "Influence factors of two dimensional position map on photomultiplier detector block designed by quadrant sharing technique", Nuclear Science and Techniques, vol. 22, pp. 224-229, Apr. 2011 (7 pages total).

(Continued)

*Primary Examiner* — Edwin C Gunberg
(74) *Attorney, Agent, or Firm* — Sughrue Mion, PLLC

(57) ABSTRACT

A computer-implemented method (200) of radiation events localizations is indicated for a pixelated radiation detector (10) having a scintillator array (24) of scintillator array elements (26) arranged in an (m)×(n) array, and an optical sensor array (28) of optical sensors (30) arranged in a (q)×(z) array and coupled to the scintillator array (24) in light sharing mode. The method includes the steps of sampling (72) spatial intensity distributions of scintillation photons emitted by the scintillator array (24) in response to multiple incident radiation events; performing a clustering analysis (76) based on the sampled spatial intensity distributions, to obtain clusters (84) of radiation events attributed to scintillator array elements (26), wherein the dimension of the sampled spatial intensity distributions correspond to the (q)×(z) dimensions of the optical sensor array (28), and determining the localization of the radiation events based on the clustering analysis (76).

15 Claims, 7 Drawing Sheets

(56) References Cited

OTHER PUBLICATIONS

Wei et al., "Crystal Identification in Dual-Layer-Offset DOI-PET Detectors Using Stratified Peak Tracking Based on SVD and Mean-Shift Algorithm", IEEE Transactions on Nuclear Science, vol. 63, No. 5, Oct. 2016, pp. 2502-2508 (7 pages total).
Lerche et al., "Maximum Likelihood Based Positioning and Energy Correction for Pixelated Solid State PET Detectors", 2011 IEEE Nuclear Science Symposium Conference Record, MIC I 8.M-8, pp. 3610-3613, 2011 (4 pages total).
Jimenez, "Analysis of positron emission tomography images for recurrence prediction of cervical cancer", Dec. 20, 2016, Retrieved from the Internet: URL:https://tel.archives-ouvertes.fr/tel-01420492/document (167 pages total).
Scheiner et al., "A Multi-Stage Clustering Framework for Automotive Radar Data", 2019 IEEE Intelligent Transportation Systems Conference (ITSC), Auckland, NZ, Oct. 27-30, 2019, pp. 2060-2067 (8 pages total).
International Search Report dated Mar. 29, 2021 from the International Searching Authority in International Application No. PCT/IB2021/050850.

\* cited by examiner

COMPUTER-IMPLEMENTED METHOD FOR IDENTIFYING AND LOCALIZING RADIATION EVENTS AND A PIXILATED RADIATION DETECTOR FOR CARRYING OUT THE METHOD

CROSS REFERENCE TO RELATED APPLICATIONS

This application is a National Stage of International Application No. PCT/IB2021/050850 filed Feb. 3, 2021, claiming priority based on European Patent Application No. PCT/IB/2021/050850 filed Feb. 3, 2021.

FIELD OF THE INVENTION

The present invention concerns a computer-implemented method for identifying and localizing radiation events and a pixelated radiation detector, like gamma ray detectors for carrying out the method. The present invention also concerns a medical imaging device comprising the pixelated radiation detector.

DESCRIPTION OF RELATED ART

Pixelated radiation detectors i.e. imaging detectors are used in nuclear medicine imaging systems, for example, in Single Photon Emission Computed Tomography (SPECT) and in Positron Emission Tomography (PET) imaging systems and in other applications. These imaging devices often use Gammy ray and X-ray imaging detectors to acquire imaging data, such as gamma ray or photon imaging data. Such imaging detectors usually acquire projections of distributions of radionuclides emitted from an object (e.g., a patient) being imaged. Scintillation detectors typically represent the imaging detectors for Gamma ray or x-ray imaging.

A scintillator crystal or an array of scintillator crystals coupled to an array of photosensitive elements form a scintillation detector. When an object is introduced in the imaging region of an imaging detector and emits photons or charged particles such as electrons, alpha particles, ions or high-energy photons, the scintillator scintillates, i.e. emits light flashes, in response to incoming particles emitted by the object. The scintillators are therefore configured to emit photons which are captured by the photosensitive element i.e. a photodetector, which, in turn, is read out by dedicated read-out electronics.

The image detectors may be rotated around a patient to acquire a plurality of projections to create a multi-dimensional image of a structure of interest or photons transmitted through the object. A non-rotatable plurality of detectors may also be used to acquire the plurality of projections as well. S. These systems are configured to provide information on where and when the respective particle was emitted, which can be exploited by medical or other imaging devices by introducing a substance emitting particles or by causing the emission of particles at certain areas in other ways. If, for example, a patient is administered a radioactive tracer emitting a certain kind of particles (possibly in response to a metabolic reaction) an image can be generated as a representation of where these particles were emitted. Alternatively, a gamma ray detector may also detect gamma rays emitted by a gamma ray source and interacting with an object (e.g. a patient) on their way to the detector. Image data representing the position on where and when scintillation photons are captured can be generated based on the intensity distribution or spatial intensity distribution of the charges on the photodetector which may also be referred to as charge distribution. In other words, a temporal and spatial position of the incident particles in the scintillator may be determined.

In modern PET scanners the spatial resolution is important, and resolution depends on various other factors such as the design of the photodetector or the scintillator, data processing, the used algorithms, the calibration of the different components, material properties (size, quality, etc.), external conditions or other influences. For instance, the spatial resolution achievable with a given detector design is dependent, to a great extent, on the size of the detector elements (e.g. size of the optical sensor array or the scintillator array in case arrays are used).

The scintillator comprised in the detector may for example, comprise a single (monolithic) block, which results in a continuous distribution of the emitted scintillation photons (light distribution) in response to incident particles to be sampled and analysed. Alternatively, the scintillator may comprise an array of small crystal elements, which results in an intrinsic spatial resolution of the imaging detector. The positions of the incident particles can be determined with higher precision if the scintillator comprises a higher number of crystal elements in a given area as this may increase the resolution. However, this leads to a higher number of crystal elements that have to be correctly identified.

One method for the identification of the crystal which interacts with an incident particle relies on dedicated photodetector elements configured to read out respective individual scintillator crystal element of an array of crystal elements. Another method is to use light-sharing with several crystal elements read out per several optical sensors. In order to identify the respective crystal element, that was hit by the incident particle, it may then be evaluated how the scintillation light is distributed over multiple photodetector elements. In order to improve the detection and correct identification of the crystal element, a lightguide, i.e. an optically transparent material, may be used for spreading the scintillation light over several optical sensor array pixels. In order to identify the scintillator array elements that have been hit, the distribution of the scintillation photons, i.e. the scintillation light or scintillation flash, over the photosensitive elements of the optical sensor array may be analysed.

Further, the energy of the incident particle can be determined. However, extraction of the correct parameters (time, energy and position of the impact) is usually more difficult if light-sharing is used instead of individually reading out each scintillator array element. On the other hand, the required number of photosensitive elements in the photodetector (photodetector pixels) and the complexity of the data acquisition system may be reduced significantly, which may lead to lower device costs.

For instance, if each scintillator crystal array element is read out individually the same number of photosensitive elements in the photodetector (photodetector pixels) and electronic channels would be required. The use of the light-sharing method can reduce the number of required photodetector pixels and electronic channels by an order of magnitude.

However, the use of light sharing might increase the computational task and time in gamma ray detectors using the light-sharing of the crystal, because the energy of an incident gamma ray has to be extracted from a set of signals from all affected photosensitive elements in the photodetector. Additionally, as the gamma ray incident has to be reconstructed from the data first, before calibration can be performed (e.g. individual scintillator-wise spectral calibration and timing calibration), this represents significant calibration hurdles.

For positioning, the most widely used method is anger-positioning, i.e. the determination of the centre-of-gravity or the centroid of the distribution. For example, Wei et al. 2011 discloses influence factors of two-dimensional positioning map on photomultiplier detector block designed by quadrant sharing technique. Or, in Wei et al. 2016 crystal identification in dual-layer-offset DOI-PET detectors using stratified peak tracking based on SVD and mean-shift algorithm is disclosed. However, this method, has drawbacks like missing signals, caused for example by the dead-time of one or more photosensitive elements. It also may suffer from imperfections like bubbles in the glue or shifts in the placement that may occur in the manufacturing process of detector elements (e.g. scintillator crystal elements may be glued together to form an array further light sharing means may be fixed with glue to the crystal array).

An alternative method is to use semi-physical modelling and optimization of the model parameters for any given incident scintillation event. For example, in Lerche et al. *Maximum Likelihood Based Positioning and Energy Correction for Pixelated Solid-State PET Detectors, Nuclear Science Symposium and Medical Imaging Conference Record*, 2011, pp. 3027-3029, the authors present an alternative method for determining the position of an incident gamma ray and extracting the respective parameters. The approach is based on the Maximum Likelihood method. The most likely photo-conversion position in a scintillator array coupled to a photodetector array in light-sharing mode is determined by comparing the resulting light distribution with predetermined distributions for different photo-conversion positions in the scintillator. The most likely position, i.e. the position corresponding to the most similar light distribution, is used as an estimate for the photo-conversion position in the scintillator of the incident gamma ray. The authors show that the resolution of medical images may be improved by using the Maximum Likelihood position estimation method.

Another solution as proposed in EP3033636, is a calibration method, wherein for a set of coincidentally emitted scintillation photons, the centre-of-gravity position and cumulative energies are determined. Then a clustering analysis is performed, in order to obtain clusters of gamma ray events attributed to a scintillator array element. By cumulating, for a cluster, the spatial intensity distributions, a cumulative spatial intensity distribution of scintillation photons in response to emitted gamma rays in the scintillator array is determined.

The centre-of-gravity positioning method as described in EP3033636 relies on a parametrization to low-dimensional data space, in particular a 2D data space or a 2D data space plus one dimension for energy which has the inconvenient property to reduce the clustering separation performance thereby having a negative impact on the accuracy of the localization of radiation events.

It is therefore an aim of the present invention to obviate or at least mitigate some of the above-mentioned disadvantages.

More particularly, an aim of the present invention is to provide a computer-implemented method, for a pixelated radiation detector, with improved clustering separation performance for better accuracy of the localization of radiation events.

BRIEF SUMMARY OF THE INVENTION

This aim is achieved by means of a computer-implemented method of radiation events localization for a pixelated radiation detector comprising at least one scintillator array of scintillator array elements arranged in an (m)×(n) array, and an optical sensor array of optical sensors arranged in a (q)×(z) array and coupled to the scintillator array in light sharing mode for determining a spatial intensity distribution of scintillation photons. The scintillation photons are emitted by the scintillator array in response to incident radiation events at photo conversion positions. The computer-implemented method comprising the steps of:

sampling spatial intensity distributions of scintillation photons emitted by the scintillator array in response to multiple incident radiation events;

performing at least one clustering analysis based on the sampled spatial intensity distributions of scintillation photons, to obtain clusters of radiation events attributed to scintillator array elements, wherein the dimension of the sampled spatial intensity distributions of the scintillation photons correspond to the (q)×(z) dimensions of the optical sensor array, and determining the localization of the radiation events based on the at least one clustering analysis.

In an embodiment, a clustering analysis is repeated based on the clusters obtained by the previously performed clustering analysis.

In an embodiment, the first and second clustering analyses use the same clustering algorithm or different clustering algorithms.

In an embodiment, the clustering analysis comprises using a standard clustering algorithm.

In an embodiment, the or each clustering analysis is based on an unsupervised Machine-Learning clustering algorithm.

In an embodiment, the or each clustering analysis is based on a density-based spatial clustering algorithm.

In an embodiment, the clustering analysis comprises the steps of defining cluster domain edges parametrizing said cluster domain edges, saving obtained parameters in a calibration data array, applying said parameters to the sampled spatial intensity distributions of scintillation photons sensed by the optical sensor array (q)×(z), and obtaining data separated into (m)×(n) domains, according to a previous calibration.

In an embodiment, the optical sensors are arranged to read out scintillation data from each scintillator element of the at least one scintillator array.

In an embodiment, the at least one clustering analysis is based on light intensity samples, to obtain clusters of radiation events attributed to a scintillator array element. The spatial intensity distributions of scintillation photons of the matrix for each scintillator array element is based on said clusters.

Another aspect of the invention relates to a pixelated radiation detector for carrying out the computer-implemented method as described above. The pixelated radiation detector comprises an region within which radiation events may occur, an device arranged to detect radiation events, and a computer operatively connected to the device. The device comprises one or more detector module arrays comprising each several detector modules and a detector module array read-out arrangement connected to read the output of each detector module array. The detector module array read-out arrangement comprises a processing unit to store and/or process acquisition data.

In an embodiment, each of the detector modules comprises several scintillator units. Each scintillator unit comprises a scintillator array having a dimension of (m)×(n), an optical sensor arrangement to detect light from the scintillator array and a scintillator unit output interface connected to a detector module read-out arrangement.

In an embodiment, the scintillator array comprises scintillator elements. At least one optical sensor of the optical sensor array is associated with two or more scintillator elements. The optical sensor array defines a (q)×(z) array which is related to the size of the scintillator array by (q)<(m) or (z)<(n), or (q)<(m) and (z)<(n).

In an embodiment, the acquisition data comprises information about the (q)×(z) dimensional intensity distribution of photons, an identifier of the optical sensor and at least one-time stamp. (q)×(z) time stamps or multiple time stamps per (q)×(z) optical sensor, providing a time and spatially sampled intensity distribution of scintillated photons may be used.

Another aspect of the invention relates to a medical imaging device comprising the pixelated radiation detector as described above.

A further aspect of the invention relates to a non-transitive, computer readable storage medium for storing instructions that when executed by a processor execute the method as described above.

BRIEF DESCRIPTION OF THE DRAWINGS

The invention will be better understood with the aid of the description of embodiments given by way of examples and illustrated by the figures, in which:

FIG. 3b shows a 2D center-of-gravity illustration of clusters obtained by a subsequent clustering analysis based on the clusters obtained by the initial clustering analysis of FIG. 3a;

FIG. 4b is a side view of FIG. 4a;

FIG. 4c shows a top view of FIG. 4a;

FIG. 5b shows a bottom view of the detector module read-out arrangement of the detector module of FIG. 5a;

DETAILED DESCRIPTION OF POSSIBLE EMBODIMENTS OF THE INVENTION

Figure 5A:
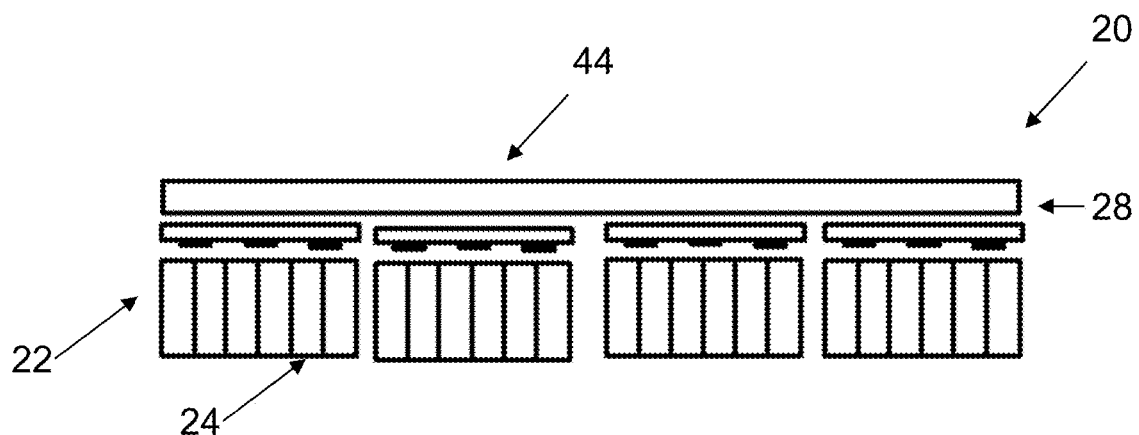
FIG. 5a shows a side view of the detector module.
Figure 5B:
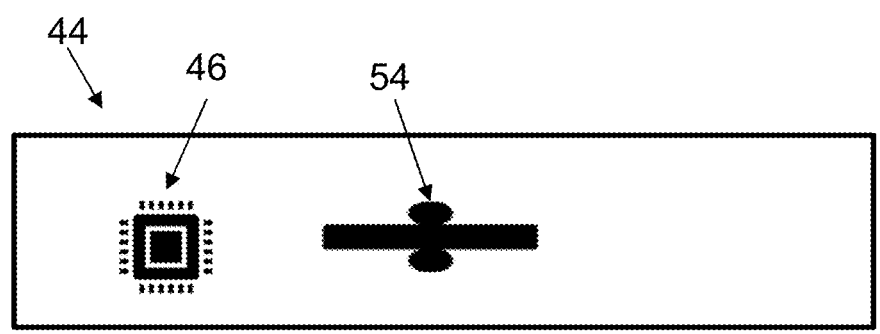
Figure 6A:
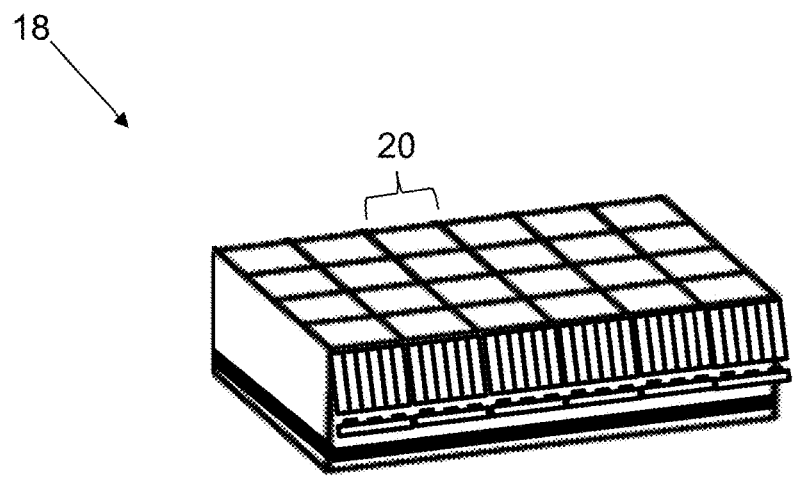
FIG. 6a shows a perspective view of the detector module array.
Figure 6B:
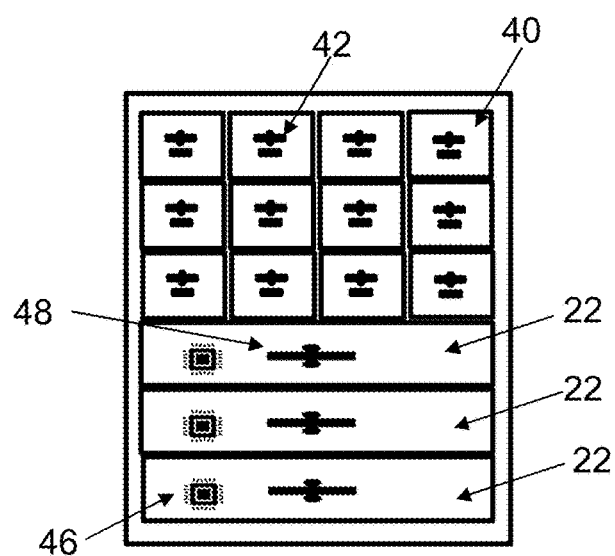
FIG. 6b shows a bottom view of the detector module array without the detector module array read-out arrangement.
Figure 6C:
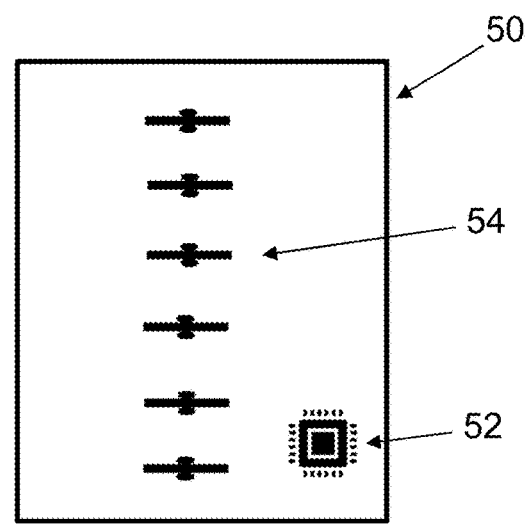
FIG. 6c shows a top view of the detector module array read-out arrangement.
Figure 7:
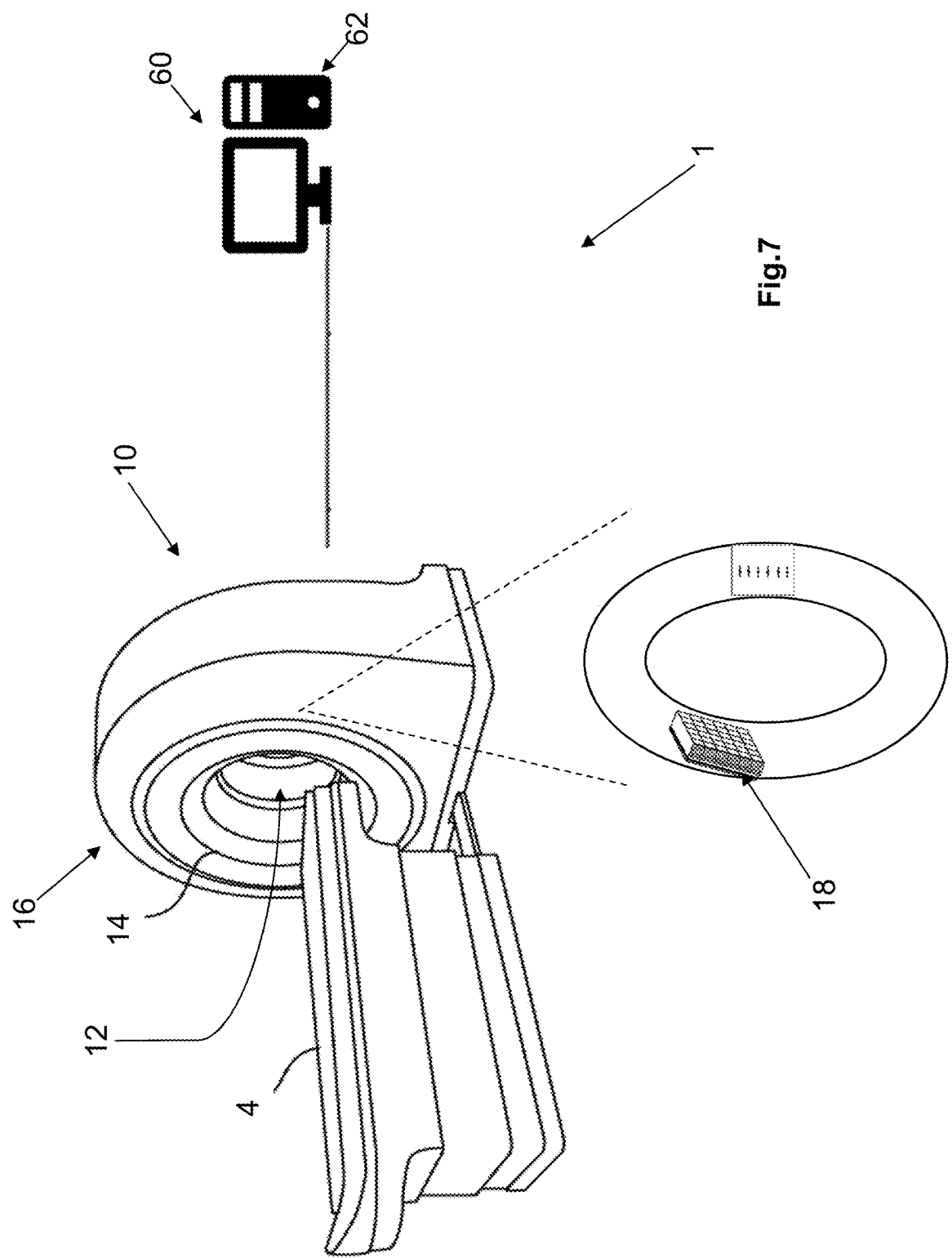
FIG. 7 shows a perspective view of a pixelated radiation detector set up for medical use.

FIG. 7 shows an embodiment of medical scanning set up system 1. The system 1 includes a positron emission tomography scanner, a pixelated radiation detector 10 one or more detector rings 16 circumscribing an imaging region 12, comprising an imaging device 14. The imaging region 12 is configured to receive the head of a subject resting on a subject support 4. The subject having received an injection with radiopharmaceuticals, starts to emit gamma rays. These gamma photons are detected by the imaging device 14 having a plurality of detector module arrays 18 mounted circumferentially on the imaging device 14. Each detector module array 18 comprises a plurality of detector modules 20 mounted on a detector module array read-out arrangement 50 as shown in FIGS. 5a and 6a-6c. The detector module array read-out arrangement 50 comprises at least one detector module array processing unit 52. In one embodiment the detector module read-out arrangement 50 is a motherboard having at least one integrated processor 52.

FIG. 6a shows an example of one detector module array 18. On FIG. 6b, the rear view is shown without the detector module array read-out arrangement. The detector module 20 comprises connectors 48 on the rear side that are connected to connectors 54 of the detector module array read-out arrangement 50 i.e. the motherboard as shown in FIG. 6c. The connectors 54 may also provide current and cooling means. One or more detector module processing units 46 are represented. In one embodiment the detector module processing unit 46 is an ASCI chip configured to store and digitalise an output data stream. Each detector module 20 comprises a plurality of scintillator units 22 mounted on the detector module 20 as shown in FIG. 5a and communicatively coupled via connectors 42 to the detector module read-out arrangement 44. FIG. 6b shows only three detector modules 20 of the array, such that the rear side of the plurality of scintillator units 22 is visible showing connectors 42. Via the connectors 42 the out-put data of optical sensors is transferred to the detector module processing unit 46 for further processing.

This modular design allows a greater versatility of the end design during manufacturing. For example, the assembly of different types of detectors in different sizes based on the same sub elements provides a faster and eventually more efficient production of medical devices integrating detector imaging systems.

Figure 4A:
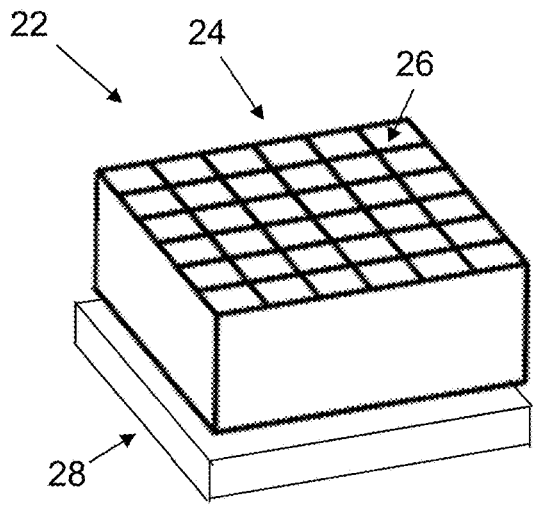
FIG. 4a shows a perspective view of a scintillator unit comprising an optical sensor array and a scintillator array.
Figure 4D:
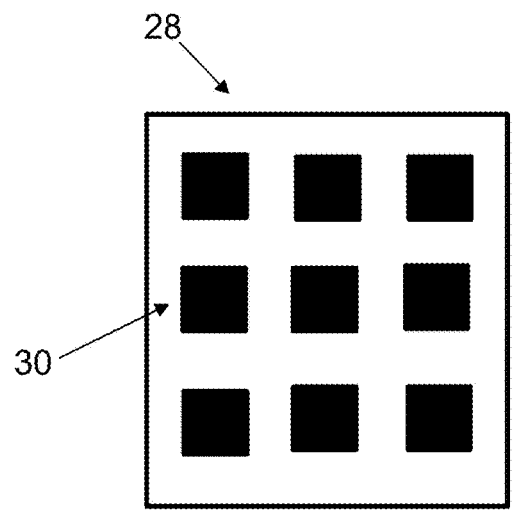
FIG. 4d shows a top view of the optical sensor array.

FIG. 4a shows an example for the scintillator unit 22 comprising a scintillator array 24 composed of (m)×(n) scintillator elements 26. In general, a scintillator is a material with the ability to absorb ionizing radiation, such as x- or gamma-rays, converting a fraction of the absorbed energy into visible or ultraviolet photons. The conversion process typically generates a short pulse of photons corresponding to each radiation event that interacts with the scintillator material. The light pulse, deposited in the scintillator element, is sensed by an optical sensor 30 within an optical sensor array 28 as shown in FIG. 4d and converted into an electrical signal. For the detection of x-rays and gamma rays, such as the 511 keV gamma rays used in PET, inorganic single-crystal scintillators 26 are used, because of their generally higher density and atomic number, which lead to better detection efficiency. The scintillator elements 26 may be for example LYSO crystal scintillators.

In other embodiments, inorganic scintillator elements such as LSO or BGO crystal may be used for the scintillator units.

Scintillators in general may be liquid or solid, organic or inorganic, and crystalline or non-crystalline. Organic liquid and plastic scintillators often are used for detection of beta particles and fast neutrons. In further embodiments, inorganic material for scintillators may be used.

Figure 4B:
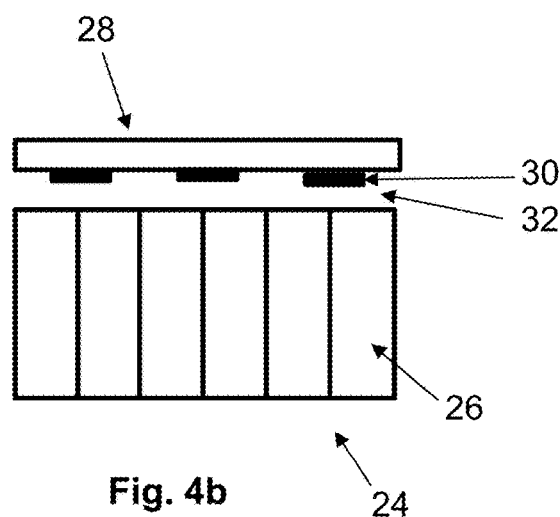
Figure 4E:
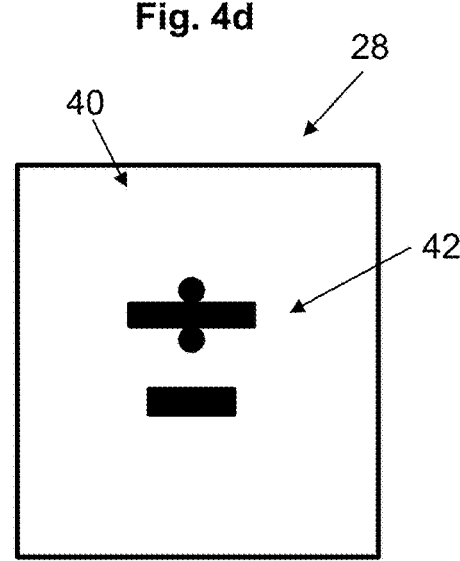
FIG. 4e shows a bottom view of the optical sensor array of FIG. 4d.
Figure 4C:
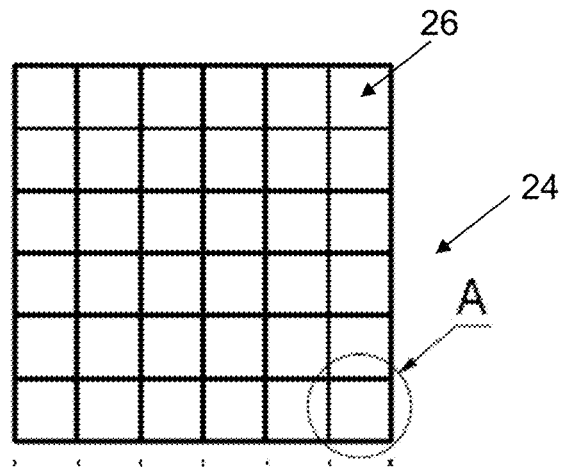
Figure 4F:
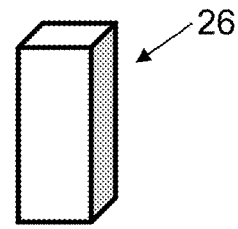
FIG. 4f shows a perspective view of a scintillator element.

In one embodiment, the scintillator elements 26 are arranged in a 6×6 array in order to form a scintillator array 24 as shown on FIG. 4c. The scintillator array 24 having a surface facing the imaging region 12 (FIG. 7), This surface is named herein top surface. The top surface is not restricted to a spatial positioning. The surface opposite the top surface of the scintillator array 24 is called the rear surface of the scintillator array. This rear surface faces the optical sensor array 28 with the optical sensors 30 as shown for example in FIG. 4b.

The optical sensors 30 of the optical sensor array 28 are arranged with respect to the scintillator array 24 in a light sharing mode. The method of light sharing is broadly used to overcome the limitation of a one to one coupling of the optical sensor with the scintillator element.

In one embodiment, one optical sensor 30 is coupled to four scintillator elements 26. In this embodiment with 6×6 i.e. 36 scintillator elements 26 with a one to four light sharing mode the optical sensor array 28 is a 3×3 array i.e. nine optical sensors 30 for 36 scintillator elements.

In other embodiments, scintillator elements with different shapes may be used, for example triangular shape where an optical sensor may cover six scintillator elements in a light sharing mode. In further embodiments, smaller scintillator elements may be used such that other coupling ratios are feasible and are within the scope of the present invention. For simplicity and comprehensive description of the present invention, a coupling ratio of one to four between an optical sensor 30 and the scintillator elements is described.

A side of the optical sensor array 28 as shown in FIGS. 4b and 4e faces the scintillator element 26 while its opposite side comprises the scintillator unit output interface 40 comprising a connector 42 for data transfer of the readout data of the optical sensors. The connector 42 may also provide current and cooling means.

The optical sensor array 28 is any suitable photo detector, for example photomultiplier (PM), microchannel plate photomultiplier tubes (MCPT) or in this exemplary embodiment a Silicon based photomultiplier (SiPM).

Optionally, a processing unit may be additionally mounted on the scintillator unit output interface 40. The processing unit at this stage would allow a pre-processing of the obtained sensor data. For example, in embodiments with a higher coupling ratio between scintillator elements and one optical sensor may require a pre-processing of the obtained sensed data by the optical sensors.

The optical sensor array 28 in light sharing mode with the scintillator array 24, is fixed on the scintillator crystal array 28 either directly or through a light guide 32 arranged in between the optical sensor array 28 and the scintillator array 24 as shown in FIG. 4b. The light guide 32 may be for example air, glass, acrylic glass, sapphire, or appropriate glue with light guiding properties.

Figure 5C:
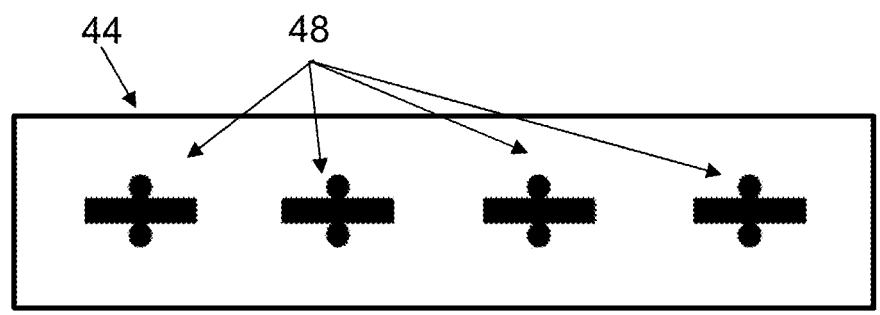
FIG. 5c shows a top view of the detector module read-out arrangement.

In one embodiment, one or more scintillator units 22 are releasably mounted on a detector module read-out arrangement 44 as shown in FIG. 5a. This detector module read-out arrangement 44 has a side facing the scintillator unit output interfaces 40 with connectors 42 (FIG. 4e). The detector module read-out arrangement 44 comprises connectors 48, as shown in FIG. 5c, coupled to the corresponding connectors 42 of the scintillator units 22. Connectors 48 provide a data transfer of the read-out data from the scintillator units 22. The connectors 48 may also provide current and cooling means.

In one embodiment, the connector 42 of each scintillator unit output interfaces 40 of four scintillator units 22 are plugged into the corresponding connectors 48 of the detector module read-out arrangement 44.

In an exemplary embodiment six detector modules 20 are mounted on a mother board 50 forming a detector module array 18 as shown in FIG. 6a-6c.

In one embodiment, one or more of these detector module arrays 18 are mounted on the detector ring 16 of the imaging device 14 of the pixelated radiation detector 10 of the medical scanning set up system 1 as shown in FIG. 7. The detector module array read-out arrangement 50 comprises connectors and mounting means for connecting the module arrays 18 to the imaging device and an external processing unit for example a computer 60.

The modular structure of the scintillator unit 20 may be seen as the unitary building block, the detector module array read-out arrangement 50 and the scintillator unit output interface 40 only need to be adapted i.e. if the detector module size or the detector module array size shall be adapted to a different architecture of a detector.

During a radiation event, a light pulse deposited in the scintillator element 26 is sensed by an optical sensor 30 within an optical sensor array 28 and converted into an electrical signal. The plurality of radiation events converted into electrical signal forms the read-out data which is processed by the method of the present invention.

Figure 1:
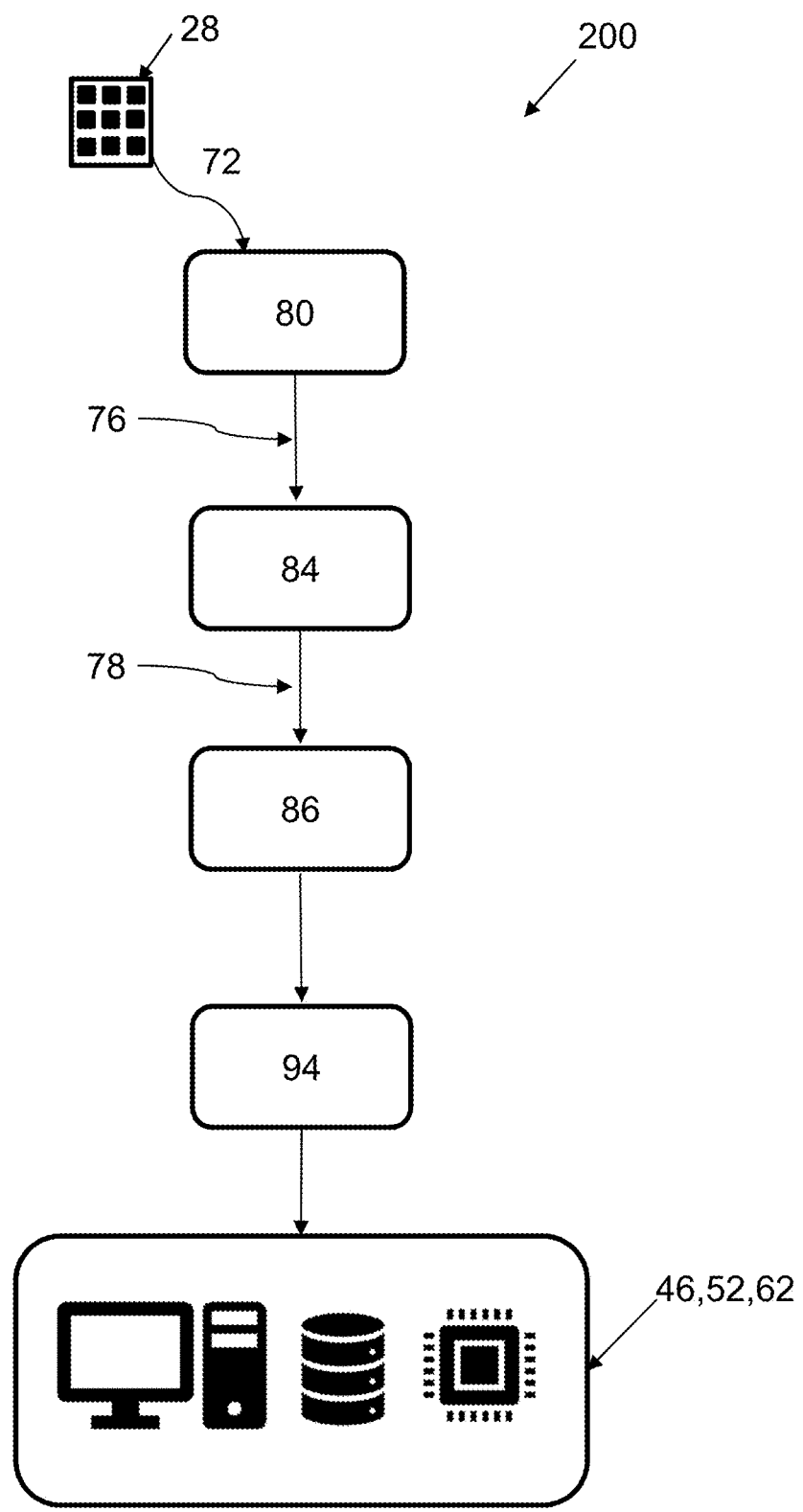
FIG. 1 shows a flowchart of the computer-implemented method for radiation events localizations.

FIG. 1 shows an exemplary flow chart of the computer implemented method 200, of the read-out data as processed to obtain a localization of the radiation event in a specific scintillator element from the obtained samples of electrical signals from the optical sensors 30 within an optical sensor array 28.

The data captured by the optical sensors 30 within an optical sensor array corresponding to radiation events in individual scintillator element 26 within respective scintillator array 24 are transferred via connectors 42 to the respective detector module processing units 46.

The detector module processing unit 46 samples 72 from the obtained data 80 spatial intensity distributions of scintillation photons emitted by the scintillator array. In one embodiment, sampling corresponds to the recording of fractions of the intensity distribution of the photons in selected positions, engineered to maximise light detection efficiency, or engineered to maximise the light-sharing separation power (i.e. the distance of the data clusters), or engineered to maximise system Time-of-Flight (ToF) capabilities, or engineered to obey certain symmetries to simplify later processing, or other methods of selecting good positions. Sampling and recording the data on each detector module processing unit 46 allows to avoid data pile-up on a centralized data processing unit. The digitalization process of the sensed analogue data may advantageously be digitalized at the detector module level.

Figure 3A:
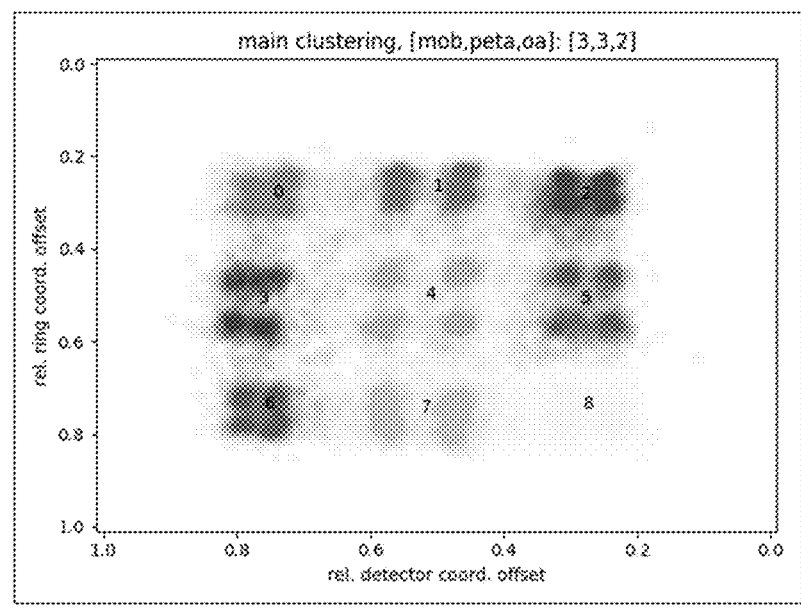
FIG. 3a shows a 2D center-of-gravity illustration of clusters obtained by an initial clustering analysis.

In one embodiment, a calibration step comprises a clustering analysis 76 performed on the sampled data to obtain a first set of clusters. An example of these obtained clusters is shown in FIG. 3a.

The sampled data is of the dimension (q)×(z)—the dimensions of the optical sensor array. The analysis comprises identifying clusters, by supervised, semi-supervised or unsupervised machine learning. This first clustering analysis provides information of the localization of the radiation events distinguishing the optical sensor which sensed the radiation event. The clusters represent also the dimensions of the optical array 28. In the exemplary embodiment, 3×3 optical array is used, i.e. 9 clusters.

The advantage of using high (q)×(z) dimensional data space, compared to a "marginalized" 2D/(2+1)D or otherwise parametrized data space, lies in retention of "more volume" in the higher dimension. This is a mathematical property of high dimensional spaces. More volume in between data points eases the separation of these data points.

Further, "cluster domain edges", are defined either by centroid, decision tree, or other methods depending on the employed supervised, semi-supervised, or unsupervised machine learning algorithm. The format of the domain edge representation depends largely on the method used for determining the clusters. The domain edges are parameterized, and these parameters are saved in a data array, i.e. a calibration data array 84.

Figure 3B:
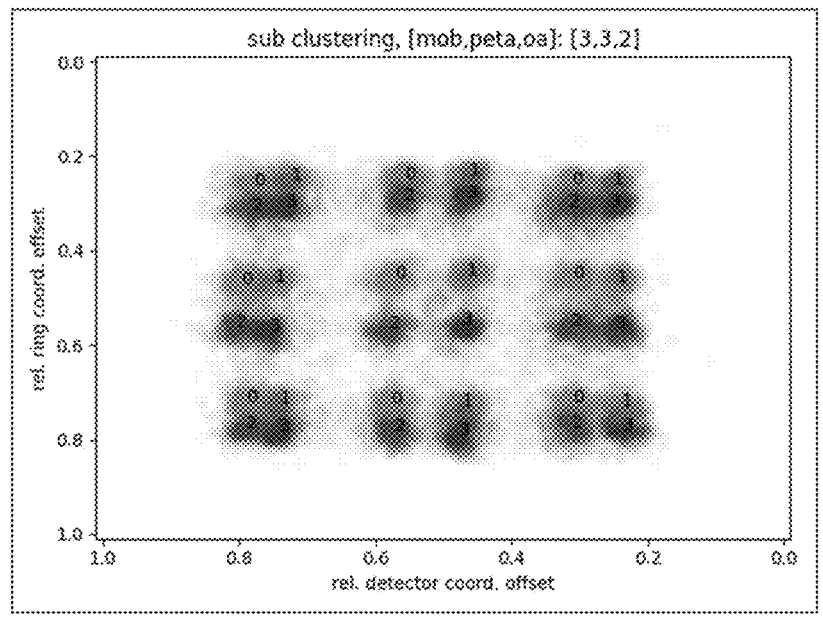

In one embodiment a second clustering analysis 78 is performed on the previous clustered data obtained by the clustering analysis 76 of the first calibration step, in order to obtain a further distinction of the radiation events. The clustering analysis 78 comprises identifying further clusters in the obtained clusters of the analysis in step 76. FIG. 3b shows the clusters in cluster analysis providing the distinction of the radiation events on the level of each scintillator crystals 26. The calibration data array 84, which contains the parametrized domain edges, is then applied in this second step to the fast (q)×(z)—dimensional data 86 directly. This gives data 94 separated into (m)×(n) domains, according to the previous calibration. Accordingly, the dimension of the obtained cluster data 86 is in total (m)×(n), or in the example embodiment 36, which corresponds to the dimension of the scintillator array 28.

In one embodiment the clustering analysis of step 76 is performed on one or more external data processing units, like an external computer, server or cloud. The obtained calibration data array 84 may be stored on detector module array processing unit 52. The clustering analysis step 78 thus can be performed also on detector module level within the detector module processing unit 52.

Figure 2:
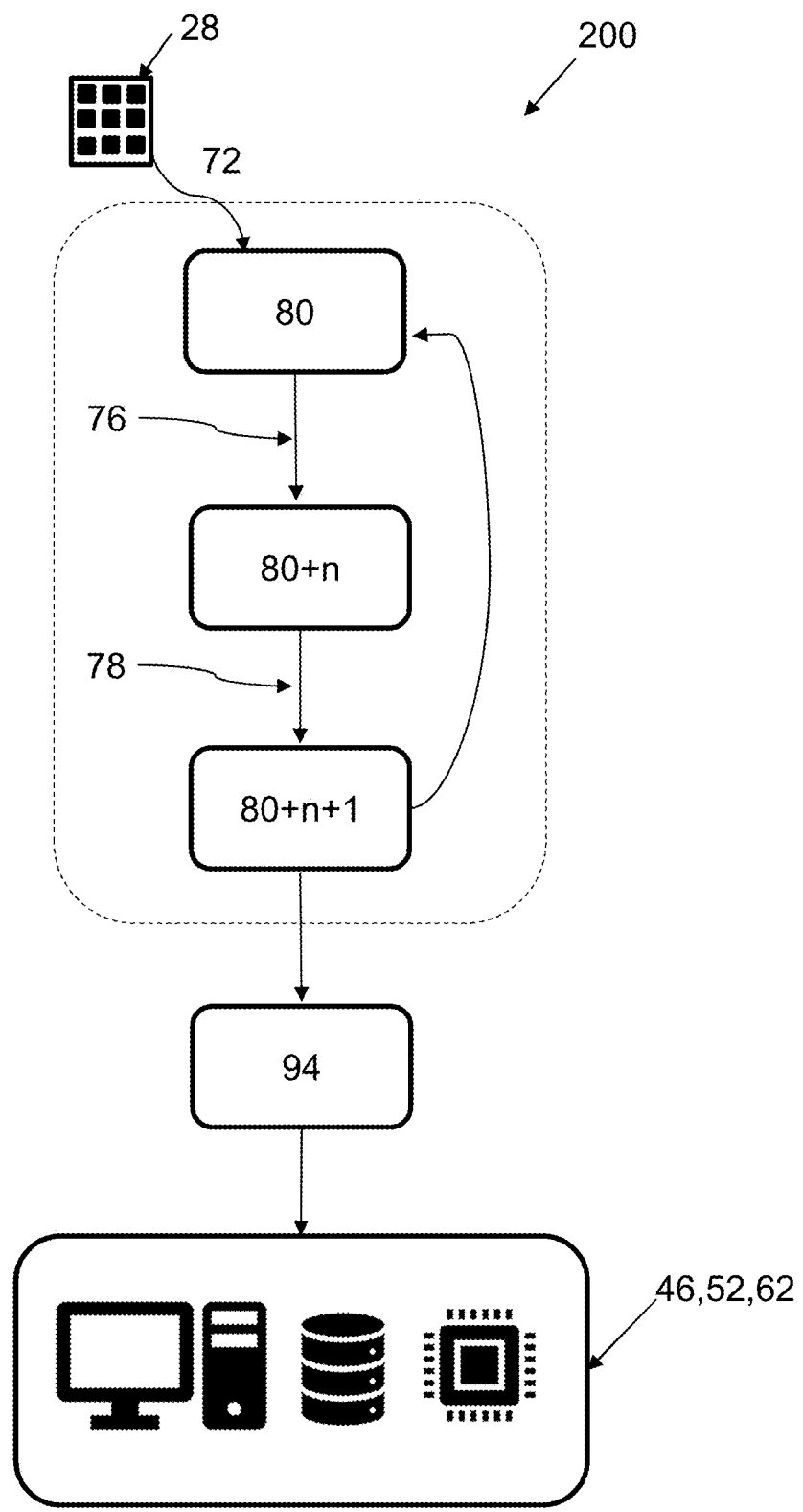
FIG. 2 shows a flowchart of the method of FIG. 1 with a feedback loop.

FIG. 2 shows an alternative embodiment with a clustering analysis performed n-times on the obtained data. These additional steps may refine the precision of the separation of the clusters and thus allow higher precision in the localization of the data associated with the radiation events. The same or a different type of clustering algorithm may be used.

The clustering analysis in step 76 and or in 78 may be based on machine learning algorithm. Although a great number of algorithms may be suitable for the computer-implemented method for the localisation of radiation events, density based and or hierarchical clustering methods have shown to be more robust while providing better results.

In one embodiment, the clustering analysis 76 and optionally the second clustering analysis 78 is/are based on a density-based spatial clustering of applications with noise (DBSCAN) algorithm.

The invention claimed is:

1. A computer-implemented method of radiation events localizations for a pixelated radiation detector comprising at least one scintillator array of scintillator array elements arranged in an (m)×(n) array, and an optical sensor array of optical sensors arranged in a (q)×(z) array and coupled to the scintillator array in light sharing mode for determining a spatial intensity distribution of scintillation photons, wherein the scintillation photons are emitted by the scintillator array in response to incident radiation events at photo conversion positions, wherein the computer-implemented method comprises the steps of:
   sampling spatial intensity distributions of scintillation photons emitted by the scintillator array in response to multiple incident radiation events,
   performing at least one clustering analysis on the sampled spatial intensity distributions of scintillation photons, to obtain clusters of radiation events attributed to scintillator array elements, wherein the dimension of the sampled spatial intensity distributions of the scintillation photons correspond to the (q)×(z) dimensions of the optical sensor array, and
   determining the localization of the radiation events based on the at least one clustering analysis.

2. The computer-implemented method according to claim 1, wherein a clustering analysis is repeated based on the clusters obtained by the previously performed clustering analysis.

3. The computer-implemented method according to claim 2, wherein the first and second clustering analyses use the same clustering algorithm or different clustering algorithms.

4. The computer-implemented method according to claim 1, wherein the clustering analysis comprises using a standard clustering algorithm.

5. The computer-implemented method according to claim 1, wherein the or each clustering analysis is based on a supervised, semi-supervised, or unsupervised Machine-Learning clustering algorithm.

6. The computer-implemented method according to claim 1, wherein the or each clustering analysis is based on a density-based spatial clustering algorithm.

7. The computer-implemented method according to claim 1, wherein the clustering analysis comprises the steps of
   defining cluster domain edges
   parametrizing said cluster domain edges,
   saving obtained parameters in a calibration data array,
   applying said parameters to the sampled spatial intensity distributions of scintillation photons sensed by the optical sensor array (q)×(z), and
   obtaining data separated into (m)×(n) domains, according to a previous calibration.

8. The computer-implemented method according to claim 1, wherein said optical sensors are arranged to read out scintillation data from each scintillator element of the at least one scintillator array.

9. The computer-implemented method according to claim 8, wherein said at least one clustering analysis is based on light intensity samples, to obtain clusters of radiation events attributed to a scintillator array element, and wherein the spatial intensity distributions of scintillation photons of the matrix for each scintillator array element is based on said clusters.

10. A pixelated radiation detector for carrying out the computer-implemented method according to claim 1, comprising an imaging region within which radiation events may occur, an imaging device arranged to detect radiation events, and a computer operatively connected to the imaging device, wherein the imaging device comprises one or more detector module arrays comprising each several detector modules and a detector module array read-out arrangement connected to read the output of each detector module array, wherein the detector module array read-out arrangement comprises a processing unit to store and/or process acquisition data.

11. The pixelated radiation detector according to claim 10, wherein each of said detector modules comprises several scintillator units, each scintillator unit comprising a scintillator array having a dimension of (m)×(n), an optical sensor arrangement to detect light from the scintillator array and a scintillator unit output interface connected to a detector module read-out arrangement.

12. The pixelated radiation detector according to claim 11, wherein the scintillator array comprises scintillator elements, wherein at least one optical sensor of the optical sensor array is associated with two or more scintillator elements, wherein the optical sensor array defines a (q)×(z) array which is related to the size of the scintillator array by (q)<(m) or (z)<(n), or (q)<(m) and (z)<(n).

13. The pixelated radiation detector module according to claim 12, wherein the acquisition data comprises information about the (q)×(z) dimensional intensity distribution of photons, an identifier of the optical sensor and at least one time stamp, possibly (q)×(z) time stamps or multiple time stamps per (q)×(z) optical sensor, providing a time and spatially sampled intensity distribution of scintillated photons.

14. Medical imaging device comprising a pixelated radiation detector for carrying out the computer-implemented method according to claim 1, the pixelated radiation detector comprising an imaging region within which radiation events may occur, an imaging device arranged to detect radiation events, and a computer operatively connected to the imaging device, wherein the imaging device comprises one or more detector module arrays comprising each several detector modules and a detector module array read-out arrangement connected to read the output of each detector module array, wherein the detector module array read-out arrangement comprises a processing unit to store and/or process acquisition data.

15. A non-transitive, computer readable storage medium for storing instructions that when executed by a processor execute the method according to claim 1.

* * * * *